(12) United States Patent
Nishimura et al.

(10) Patent No.: US 11,891,472 B2
(45) Date of Patent: Feb. 6, 2024

(54) COMPOSITION, PRODUCTION METHOD FOR COMPOSITION, AND PRODUCTION METHOD FOR UNSATURATED COMPOUND

(71) Applicant: SHOWA DENKO K. K., Tokyo (JP)

(72) Inventors: Norihito Nishimura, Kawasaki (JP); Katsutoshi Ohno, Aizuwakamatsu (JP)

(73) Assignee: RESONAC CORPORATION, Tokyo (JP)

( * ) Notice: Subject to any disclaimer, the term of this patent is extended or adjusted under 35 U.S.C. 154(b) by 493 days.

(21) Appl. No.: 17/269,147

(22) PCT Filed: Aug. 16, 2019

(86) PCT No.: PCT/JP2019/032135
§ 371 (c)(1),
(2) Date: Feb. 17, 2021

(87) PCT Pub. No.: WO2020/040049
PCT Pub. Date: Feb. 27, 2020

(65) Prior Publication Data
US 2022/0119585 A1 Apr. 21, 2022

(30) Foreign Application Priority Data
Aug. 20, 2018 (JP) ................. 2018-154146

(51) Int. Cl.
| C07C 263/10 | (2006.01) |
| C08G 18/81 | (2006.01) |
| C08G 18/10 | (2006.01) |
| C08G 18/28 | (2006.01) |
| C08G 18/48 | (2006.01) |
| C08G 18/80 | (2006.01) |

(52) U.S. Cl.
CPC .......... *C08G 18/8116* (2013.01); *C08G 18/10* (2013.01); *C08G 18/286* (2013.01); *C08G 18/288* (2013.01); *C08G 18/4833* (2013.01); *C08G 18/807* (2013.01)

(58) Field of Classification Search
CPC ... C07C 269/02; C07C 271/16; C07C 263/10; C07C 231/10; C07C 233/18; C07C 271/60; C07C 273/18; C07C 275/10
See application file for complete search history.

(56) References Cited

U.S. PATENT DOCUMENTS

| 2,821,544 A | 1/1958 | Holtschmidt et al. | |
| 4,709,087 A * | 11/1987 | Tkatchenko | C07D 213/75 |
| | | | 560/339 |
| 5,817,860 A * | 10/1998 | Rizk | C08G 18/8009 |
| | | | 560/115 |
| 7,632,965 B2 * | 12/2009 | Nozawa | C07C 263/20 |
| | | | 560/213 |
| 2011/0105654 A1 * | 5/2011 | Dicke | C08G 12/32 |
| | | | 564/60 |
| 2012/0232183 A1 | 9/2012 | Ooga et al. | |

FOREIGN PATENT DOCUMENTS

| CN | 1293684 A | 5/2001 |
| CN | 1934075 A | 3/2007 |
| CN | 105884654 A | 8/2016 |
| EP | 1 745 013 B1 | 9/2012 |
| JP | 55-017357 A | 2/1980 |
| JP | 60-234582 A | 11/1985 |
| JP | 60-234583 A | 11/1985 |
| JP | 64-042462 A | 2/1989 |
| JP | 6-184256 A | 7/1994 |
| JP | 6-187822 A | 7/1994 |
| JP | 6-322051 A | 11/1994 |
| JP | 2002-507642 A | 3/2002 |
| JP | 2006-232797 A | 9/2006 |
| JP | 2007-008828 A | 1/2007 |
| JP | 4273531 B2 | 6/2009 |
| JP | 4823546 B2 | 11/2011 |
| JP | 2016-150922 A | 8/2016 |
| KR | 10-2016-0101856 A | 8/2016 |
| TW | 201026650 A1 | 7/2010 |
| WO | 99/48943 A1 | 9/1999 |
| WO | 2011/074503 A1 | 6/2011 |

OTHER PUBLICATIONS

Communication dated Dec. 2, 2021, issued by the Taiwan Intellectual Property Office in application No. 109140522.
CMC Technical Library, "Total Technology of Polymer Stabilization", CMC Publishing Co., Ltd., Apr. 2005, 5 pgs.
Taiwanese Office Action for Application No. 108129206 dated Aug. 17, 2020.
International Search Report for PCT/JP2019/032135 dated Nov. 5, 2019 (PCT/ISA/210).
"Isocyanate (Adhesives)", Korea Wood Newspaper, Aug. 23, 2004, https://www.woodkorea.co.kr/news/articleView.html?idxno=4371.

\* cited by examiner

*Primary Examiner* — Michael M Dollinger
(74) *Attorney, Agent, or Firm* — Sughrue Mion, PLLC

(57) ABSTRACT

The composition comprises a compound (A) represented by general formula (1) and a compound (B) represented by general formula (2), and comprises 0.00002 to 2.0 parts by mass of the compound (B) with respect to 100 parts by mass of the compound (A),

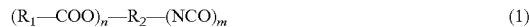 (1)

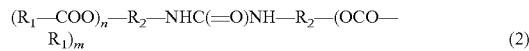

(2)

wherein in general formulae (1) and (2), $R_1$ is an ethylenically unsaturated group having 2 to 7 carbon atoms; $R_2$ is a (m+n)-valent hydrocarbon group having 1 to 7 carbon atoms and optionally contain an ether group; $R_1$ and $R_2$ in the general formula (1) are the same as $R_1$ and $R_2$ in the general formula (2); and n and m each represent an integer of one or two.

10 Claims, No Drawings

COMPOSITION, PRODUCTION METHOD FOR COMPOSITION, AND PRODUCTION METHOD FOR UNSATURATED COMPOUND

CROSS REFERENCE TO RELATED APPLICATIONS

This application is a National Stage of International Application No. PCT/JP2019/032135 filed Aug. 16, 2019, claiming priority based on Japanese Patent Application No. 2018-154146 filed Aug. 20, 2018.

TECHNICAL FIELD

The invention is related to a composition containing an unsaturated isocyanate compound, a method of producing the composition, and a method of producing an unsaturated compound.

This application claims priority under Japanese Patent Application No. 2018-154146 filed Aug. 20, 2018, the contents of which are incorporated herein by reference.

BACKGROUND TECHNOLOGY

Conventionally, a unsaturated compound such as an unsaturated urethane compound, an unsaturated thiourethane compound, an unsaturated urea compound, and an unsaturated amide compound, is produced by reacting an unsaturated isocyanate compound with a compound having active hydrogen (the compound having functional group having active hydrogen). The unsaturated compound thus produced is used in various applications.

For example, there is an unsaturated urethane compound produced by reacting 2-methacryloyloxyethyl isocyanate (Hereinafter, this may be referred to as "MOI". An example of a specific product is "KarenzMOI (registered trademark)".) which is an unsaturated isocyanate compound with a polyalkylene glycol which is a compound having a hydroxyl group. There are known methods for producing the unsaturated isocyanate compound, such as a method for reacting an amine having an ethylenic double bond with phosgene to decompose the amine by heating (for example, see Patent Document 1). The unsaturated urethane compound is proposed to be used as a material for contact lenses (for example, see Patent Document 2), a material for solid solvents of polymer solid electrolytes (for example, see Patent Document 3.), and a material for immobilizing biological materials (for example, refer to Patent Documents 4 and 5).

Further, Patent Document 6 discloses an unsaturated urea compound obtained by reacting MOI with an organopolysiloxane having amino groups at both ends of the molecule. Patent Document 6 discloses using the unsaturated urea compound as a material for a radiation-curable adhesive organopolysiloxane composition.

Patent Document 7 discloses a urethane acrylate synthesized by reacting an unsaturated isocyanate compound such as MOI with a product obtained by reacting a dimer diol with a polyisocyanate. Further, Patent Document 7 discloses a curable composition containing the urethane acrylate.

Examples of the unsaturated isocyanate compound used as a material of the unsaturated compound include acryloyloxyethyl isocyanate (Hereinafter, this may be referred to as "AOI". An example of a specific product is "KarenzAOI (registered trademark)".) and methacryloyl isocyanate (Hereinafter referred to as "MAI".) in addition to MOI. MOI, AOI, and MAI are industrially manufactured, commercially available, and readily available.

MOI is synthesized by the reaction of isopropenyloxazoline or 2-aminoethyl methacrylate hydrochloride with phosgene. AOI is synthesized by the reaction of 2-vinyloxazoline or 2-aminoethylacrylate hydrochloride with phosgene. MAI is synthesized by the reaction of methacrylic amide with oxalyl chloride.

The unsaturated isocyanate compound synthesized as described above includes impurities such as by-products and catalyst residues. For this reason, after the unsaturated isocyanate compound is synthesized, an operation for removing impurities to increase the purity is generally performed (for example, see Patent Documents 8 and 9.).

The synthesized unsaturated isocyanate compound is conventionally determined by various methods. Specifically, there are a method for confirming the appearance of the unsaturated isocyanate compound such as the presence or absence of turbidity and hue, a method for confirming the purity of the unsaturated isocyanate compound by using gas chromatography, a method for confirming the hydrolyzable chlorine content in the unsaturated isocyanate compound by potentiometric titration, and a method for confirming a soluble impurity in the unsaturated isocyanate compound by using gel permeation chromatography (GPC) (See, for example, Patent Document 10.).

Generally, in order to stably transport and store the unsaturated isocyanate compound, a polymerization inhibitor is added to the unsaturated isocyanate compound. As the polymerization inhibitor, hydroquinone or the like is used and is added at a concentration of several tens to several hundred ppm. For example, Patent Document 7 discloses that, when an unsaturated urethane compound is synthesized using an unsaturated isocyanate compound, a polymerization inhibitor is added in an amount of 0.01 to 10 parts by mass based on 100 parts by mass of the total weight components.

PATENT DOCUMENTS

[Patent Document 1] U.S. Pat. No. 2,821,544
[Patent Document 2] Japanese Patent Laid-Open No. H06-322051
[Patent Document 3] Japanese Patent Laid-Open No. H06-187822
[Patent Document 4] Japanese Patent Laid-Open No. S60-234582
[Patent Document 5] Japanese Patent Laid-Open No. S60-234583
[Patent Document 6] Japanese Patent Laid-Open No. H06-184256
[Patent Document 7] WO 2011/074503
[Patent Document 8] Japanese Patent No. 4273531
[Patent Document 9] Japanese Patent No. 4823546
[Patent Document 10] Japanese Patent Laid-Open No. 2007-8828

NON-PATENT DOCUMENTS

[Non-Patent Document 1] CMC Technical Library "Polymer degradation mechanism and stabilization technology" CMC Publishing Co., Ltd. (Issued on 2005/04) Page 168, FIG. 5.

SUMMARY OF THE INVENTION

Conventional unsaturated isocyanate compounds may cause unexpected viscosity increases or gelation during storage and/or transport, even though there is no significant difference in quality by using conventional determination methods. Therefore, it has been required to improve the stability during storage.

In addition, the conventional unsaturated isocyanate compound does not show a large difference in quality by using the conventional determination method, but when the unsaturated compound is produced by using the same, the viscosity of the reaction product is sometimes rapidly increased or gelatinized during production. Therefore, it has been required to improve the stability in use.

In order to improve the storage stability and the utilization stability of the unsaturated isocyanate compound, a sufficient amount of a polymerization inhibitor may be added to the unsaturated isocyanate compound.

However, when a large number of polymerization inhibitors are added to an unsaturated isocyanate compound, a colored component caused by the polymerization inhibitor is easily generated together with the unsaturated compound when the unsaturated compound is produced using the unsaturated isocyanate compound as a raw material (for example, see Non-patent Document 1.). Therefore, the produced unsaturated compound may be colored.

An object of the present invention is to provide a composition excellent in stability during storage and stability during use, and a method of producing the composition.

Means to Solve the Problem

In order to solve the above problems, the present inventors have diligently investigated. As a result, it was found that a compound having a specific structure (hereinafter referred to as "specific compound") contained as an impurity in the unsaturated isocyanate compound after purification is one of the causes of deterioration of the storage stability and the stability during use of the unsaturated isocyanate compound. Further, the inventors of the present invention have repeatedly studied and found that the concentration of the specific compound in the unsaturated isocyanate compound has a correlation with the viscosity increase and the occurrence of gelation of the unsaturated isocyanate compound during storage.

However, a purification process for removing the specific compound from the unsaturated isocyanate compound has not been known. Therefore, the present inventors have studied a purification process for removing the specific compound from an unsaturated isocyanate compound. As a result, it was found that the specific compound can be removed from the unsaturated isocyanate compound by purification by using a distillation process at a reflux ratio of 2.0 to 4.0, a pressure of 1.0 to 10.0 kPa, and a distillation temperature of 90 to 140° C.

Further, the inventors examined the viscosity increase and gelation during storage of the unsaturated isocyanate compound purified by the distillation process at the reflux ratio, the pressure and the distillation temperature. As a result, it has been found that the viscosity increase and gelation can be suppressed by setting the concentration of the specific compound in the unsaturated isocyanate compound to 2.0 parts by mass or less with respect to 100 parts by mass of the unsaturated isocyanate compound.

The inventors have also found that even if the specific compound in the unsaturated isocyanate compound is sufficiently removed by the distillation process, the specific compound in the unsaturated isocyanate compound increases when the purified product obtained by the distillation process comes into contact with water. Further, the present inventors have found that the increase of the specific compound in the composition after production can be effectively suppressed by performing a vacuum breaking step in which dry nitrogen gas having a dew point of −30° C. or lower is supplied into the distillation apparatus after the distillation process and the pressure in the distillation apparatus is returned to the atmospheric pressure, and a filling step in which the purified product in the distillation apparatus after the distillation process is stored in a container and the gas phase portion in the container is filled with dry nitrogen gas having a dew point of −30° C. or lower.

In other words, the present invention relates to the following matters.

The composition according to the first embodiment of the present invention is the following composition.

[1] A composition comprising a compound (A) represented by general formula (1) and a compound (B) represented by general formula (2);

the composition contains 0.00002 to 2.0 parts by mass of the compound (B) with respect to 100 parts by mass of the compound (A).

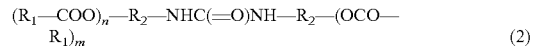

(In general formulae (1) and (2), $R_1$ is an ethylenically unsaturated group having 2 to 7 carbon atoms. $R_2$ a (m+n)-valent hydrocarbon group having 1 to 7 carbon atoms and optionally comprises an ether group. $R_2$ may contain an ether group. $R_1$ and $R_2$ of the general formula (1) are the same as $R_1$ and $R_2$ of the general formula (2). n and m are integers of 1 or 2.)

The composition of the first embodiment of the present invention also preferably has the following features [2] to [5]. These features are preferably combined.

[2] The compound (A) may be at least one compound selected from the group consisting of 2-methacryloyloxyethyl isocyanate, 2-(isocyanatoethyloxy) ethyl methacrylate, 2-acryloyloxyethyl isocyanate, 2-(isocyanatoethyloxy) ethyl acrylate, and 1,1-bis(acryloyloxymethyl)ethyl isocyanate.

[3] The content of the compound (A) may be 95.0% by mass or more.

[4] The content of the compound (A) may be from 97.0% by mass to 99.9% by mass.

[5] As an additive, the composition may further contain any one selected from the group consisting of the group consisting of hydroquinone, methoxyhydroquinone, catechol, p-tert-butylcatechol, cresol, 2,6-di-tert-butyl-4-methylphenol (BHT), and phenothiazine.

The second embodiment of the present invention is a method of producing the following composition.

[6] The method includes a step of producing a mixture which comprises a compound (A) represented by general formula (1) and a compound (B) represented by general formula (2) and which comprises more than 2.0 parts by mass of the compound (B) with respect to 100 parts by mass of the compound (A); and purifying the mixture by a distillation process at a reflux ratio of 2.0 to 4.0, a pressure of 1.0 to 10.0 kPa and a distillation temperature of 90 to 140° C., wherein the purifying step comprises a vacuum breaking step of supplying dry nitrogen gas having a dew point of −30° C. or lower into a distillation apparatus after distillation process and returning the pressure in the distillation apparatus to atmospheric pressure, and a filling step of storing the purified product in the distillation apparatus after the distillation process in a container and filling the gas phase portion in the container with dry nitrogen gas having a dew point of −30° C. or lower.

$$(R_1—COO)_n—R_2—(NCO)_m \quad (1)$$

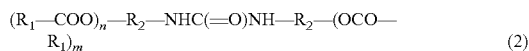

$$(R_1—COO)_n—R_2—NHC(=O)NH—R_2—(OCO—R_1)_m \quad (2)$$

(In general formulae (1) and (2), $R_1$ is an ethylenically unsaturated group having 2 to 7 carbon atoms. $R_2$ a (m+n)-valent hydrocarbon group having 1 to 7 carbon atoms and optionally comprises an ether group. $R_2$ may contain an ether group. $R_1$ and $R_2$ of the general formula (1) are the same as $R_1$ and $R_2$ of the general formula (2). n and m are integers of 1 or 2.)

The method of producing the composition according to the second embodiment of the present invention also preferably has the following features (7) to [10]. It is also preferable to combine them.

[7] In the composition obtained by the purifying step, a content of the compound (B) with respect to 100 parts by mass of the compound (A) is 0.00002 to 2.0 parts by mass.

[8] $R_1$ is $CH_2=C(CH_3)—$ or a vinyl group in the general formulae (1) and (2).

[9] The dry nitrogen gas supplied in the vacuum breaking step and the dry nitrogen gas filled in the filling step have a dew point of −70° C. or higher.

[10] When performing the distillation process in the purifying step, the method may include a step of adding, as an additive to the mixture, any one selected from the group consisting of hydroquinone, methoxyhydroquinone, catechol, p-tert-butylcatechol, cresol, 2,6-ditert-butyl-4-methylphenol (BHT), and phenothiazine before starting to heat the mixture.

A third embodiment of the present invention is a method of producing the following unsaturated compounds.

[11] A method of producing an unsaturated compound, comprising the steps of: mixing the composition described in [1] or [2] with a compound having active hydrogen; and reacting the compound (A) contained in the composition with the compound having active hydrogen to obtain a reaction product.

It is also preferable that the producing method according to the third embodiment of the present application has the following features [12] to [15]. These features are preferably combined.

[12] The compound having the active hydrogen is an alcohol, a thiol, an amine or a carboxylic acid.

[13] The reaction product may be an unsaturated urethane compound, an unsaturated thiourethane compound, an unsaturated urea compound, or an unsaturated amide compound.

[14] The reaction product may be any one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

[15] The reaction temperature at which the compound (A) contained in the composition is reacted with the compound having the active hydrogen is −10 to 100° C.

Effect of the Invention

The composition comprises a compound (A) represented by general formula (1) and a compound (B) represented by general formula (2), wherein with respect to 100 parts by mass of the compound (A), 0.00002 to 2.0 parts by mass of the compound (B) are contained. Therefore, unexpected viscosity increase and gelation of the composition unlikely occur during storage and transportation, and stability during storage is excellent. The composition of the present invention unlikely causes a rapid increase in viscosity or gelation of a reaction product generated during production when an unsaturated compound is produced by using the composition, and is excellent in stability in use.

The composition of the present invention is excellent in stability during storage and stability during use. Therefore, it is not necessary to contain a large amount of a polymerization inhibitor which produces a colored component. Therefore, it is possible to prevent the unsaturated compound produced by using the composition of the present invention from being colored by the coloring component caused by the polymerization inhibitor.

The method of producing the composition which contains more than 2.0 parts by mass of the compound (B) with respect to 100 parts by mass of the compound (A), by purifying the mixture by a distillation process at a reflux ratio of 2.0 to 4.0, a pressure of 1.0 to 10.0 kPa, and a distillation temperature of 90 to 140° C. to obtain a purified product containing 0.00002 to 2.0 parts by mass of the compound (B) with respect to 100 parts by mass of the compound (A). Accordingly, the composition of the present invention, from which the compound (B) affecting the stability during storage and affecting the stability during use is sufficiently removed, can be produced in high yield.

In the method of producing the composition, the purifying step comprises a vacuum breaking step of supplying dry nitrogen gas having a dew point of −30° C. or lower into a distillation apparatus after the distillation process and returning the pressure in the distillation apparatus to atmospheric pressure, and a filling step of storing the purified product in the distillation apparatus after the distillation process in a container and filling a gas phase portion in the container with dry nitrogen gas having a dew point of −30° C. or lower. Therefore, the compound (A) in the purified product after the distillation process is unlikely brought into contact with water, and the compound (B) is unlikely increased in the composition after production. Therefore, according to the method of producing the composition of the present invention, a composition having good stability during storage and stability during use can be obtained.

The method of producing the unsaturated compound includes steps of mixing the composition of the invention with a compound having active hydrogen and reacting the compound (A) contained in the composition with the compound having active hydrogen to obtain a reaction product. In the method of producing the unsaturated compound of the present invention, since the composition used as a material contains 0.00002 to 2.0 parts by mass of the compound (B) with respect to 100 parts by mass of the compound (A), rapid increase in viscosity or gelation of the reaction product is unlikely generated during production, and excellent productivity is obtained.

MODE FOR CARRYING OUT THE INVENTION

Preferred examples of the present invention will be described below.

It should be noted that the following examples are specifically described for better understanding of the purpose of the invention, and the invention is not limited to these examples unless otherwise specified. Within the scope of the present invention, amounts, types, ratios, numbers, locations, and the like may be omitted, changed, replaced, and/or added as needed.

The pressure described herein is an absolute pressure.

"Composition"

The composition of this embodiment contains an unsaturated isocyanate compound. The composition of this embodiment comprises a compound (A) represented by general formula (1) and a compound (B) represented by general formula (2). The composition of the present embodiment preferably has a content of the compound (A) of 95.0% by mass or more, but is not limited to this example. The composition of the present embodiment contains 0.00002 to 2.0 parts by mass of the compound (B) with respect to 100 parts by mass of the compound (A).

(1)

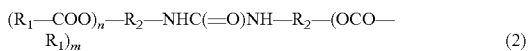
(2)

(In general formulae (1) and (2), $R_1$ is an ethylenically unsaturated group having 2 to 7 carbon atoms. $R_2$ is a (m+n)-valent hydrocarbon group having 1 to 7 carbon atoms and optionally contain an ether group. $R_1$ and $R_2$ of the general formula (1) are the same as $R_1$ and $R_2$ of the general formula (2). And, n and m are integers of 1 or 2.)

In general formulae (1) and (2), $R_1$ is an ethylenically unsaturated group having 2 to 7 carbon atoms. The ethylenically unsaturated bond of $R_1$ may be one or two or more. When the number of carbon atoms is 6 or more, the reactivity of the ethylenically unsaturated group is lowered, so that $R_1$ is preferably an ethylenically unsaturated group having 2 to 5 carbon atoms. The carbon number is preferably 2 to 3 or 4 to 5. Among the ethylenically unsaturated groups having 2 to 5 carbon atoms, $R_1$ is preferably $CH_2=C(CH_3)-$ or a vinyl group because the raw material is easily available.

In the formulae (1) and (2), $R_2$ is an m+n valent hydrocarbon group having 1 to 7 carbon atoms and the hydrocarbon group may be a linear or branched chain. The carbon number of the m+n valent hydrocarbon group represented by $R_2$ is preferably any one of 2 to 4, and more preferably 2. $R_2$ may contain an ether group. $R_2$ is preferably an ethylene group, a methylene group, or $-CH_2CH_2OCH_2CH_2-$ in view of the availability of the raw materials.

$R_1$ of the general formula (1) is the same as $R_1$ of the general formula (2) and $R_2$ of the general formula (1) is the same as $R_2$ of the general formula (2).

In general formulae (1) and (2), n and m are integers of 1 or 2, and both are preferably 1 in view of ease of synthesis.

As the compound (A) represented by general formula (1), for example, at least one compound selected from the group consisting of 2-methacryloyloxyethyl isocyanate, 3-methacryloyloxy-n-propyl isocyanate, 2-methacryloyloxyisopropyl isocyanate, 4-methacryloyloxy-n-butyl isocyanate, 2-methacryloyloxy-tert-butyl isocyanate, 2-methacryloyloxybutyl-4-isocyanate, 2-methacryloyloxybutyl-3-isocyanate, 2-methacryloyloxybutyl-2-isocyanate, 2-methacryloyloxybutyl-1-isocyanate, 5-methacryloyloxy-n-pentyl isocyanate, 6-methacryloyloxy-n-hexyl isocyanate, 7-methacryloyloxyn-heptylisocyanate, 2-(isocyanatoethyloxy) ethyl methacrylate, 3-methacryloyloxyphenyl isocyanate, 2-acryloyloxyethyl isocyanate, and 2-acryloyloxyisocyanate, 3-acryloyloxy-n-propyl isocyanate, 2-acryloyloxyisopropyl isocyanate, 4-acryloyloxy-n-butyl isocyanate, 2-acryloyloxy-tert-butyl isocyanate, 2-acryloyloxybutyl-4 isocyanate, 2-acryloyloxybutyl-3-isocyanate, 2-acryloyloxybutyl-2-isocyanate, 2-acryloyloxybutyl-1-isocyanate, 5-acryloyloxy-n-pentyl isocyanate, 6-acryloyloxy-n-hexyl isocyanate, 7-acryloyloxy-n-heptyl isocyanate, 2-(isocyanatoethyloxy) ethyl acrylate, 3-acryloyloxyphenyl isocyanate, 4-acryloyloxyphenyl isocyanate, 1,1-bis(methacryloyloxymethyl) methyl isocyanate, 1,1-bis(methacryloyloxymethyl) ethyl isocyanate, 1,1-bis(acryloyloxymethyl) methyl isocyanate, 1,1-bis(acryloyloxymethyl) ethyl isocyanate, and 2'-pentenoyl-4-oxyphenyl isocyanate is used. Among these compounds, especially in view of ease of synthesis and availability of raw materials, the compound (A) is preferably 2-methacryloyloxyethyl isocyanate (examples of specific products: KarenzMOI (registered trademark)), 2-acryloyloxyethyl isocyanate (example of specific product: KarenzMOI (registered trademark)), 2-(isocyanatoethyloxy)ethyl methacrylate (example of specific product: KarenzMOI-EG (registered trademark)), 2-(isocyanatoethyloxy)ethyl acrylate (example of specific product: KarenzAOI-EG), or 1,1-bis(methacryloyloxymethyl)ethyl isocyanate (example of specific product: KarenzBEI (registered trademark)). It should be noted that the products including Karenz in the registered trademark described herein are available from Showa Denko K.K.

The content of the compound (A) in the composition of this embodiment is preferably 95.0% by mass or more, more preferably 97.0% by mass or more, and more preferably 98.0% by mass to 99.9% by mass. The content may be from 96.00% by mass to 99.99% by mass or from 97.00% by mass to 99.50% by mass, if necessary.

When the content of the compound (A) in the composition is 95.0% by mass or more, it can be suitably used as a raw material for producing an unsaturated compound. When the content of the compound (A) is 99.9% by mass or less, the composition can be efficiently produced by a method of purification by distillation process, which is preferable. The content of the compound (A) in the composition of the present embodiment is not limited to the above, and can be optionally selected as necessary. For example, the amount of the lower limit of the content of the compound (A) may be 1.0% by mass or more, 10% by mass or more, 30% by mass or more, 50% by mass or more, 70% by mass or more, or 80% by mass or more.

In the compound (B) represented by the general formula (2), $R_1$ and $R_2$ of the general formula (1) and the general formula (2) are the same. The compound (B) represented by the general formula (2) is presumed to be an impurity which is by-produced when the compound (A) represented by the general formula (1) is produced by a production method described later. The compound (B) degrades the stability of the composition during storage and utilization.

In the present embodiment, with respect to 100 parts by mass of the compound (A), 0.00002 to 2.0 parts by mass of the compound (B) are contained in the composition. Since the content of the compound (B) with respect to 100 parts by mass of the compound (A) in the composition is 2.0 parts by mass or less, excellent stability in storage and stability in use can be obtained. The content of the compound (B) with respect to 100 parts by mass of the compound (A) in the composition is preferably 1.0 parts by mass or less, and more preferably 0.5 parts by mass or less. The stability during storage and the stability during use can be further improved by setting the content of the compound (B) with respect to 100 parts by mass of the compound (A) in the composition within the above-mentioned range. Further, since the content of the compound (B) with respect to 100 parts by mass of the compound (A) in the composition is 0.00002 parts by mass or more, a yield in producing the compound (A) can be ensured, and the composition can be produced in a high yield. The content of the compound (B) with respect to 100 parts by mass of the compound (A) in the composition is preferably 0.0002 parts by mass or more in order to further improve the yield of the compound (A).

The composition of the present invention may contain an additive in addition to the compound (A) and the compound (B) to the extent that the effect of the present invention is not impaired.

Examples of additives include polymerization inhibitors such as hydroquinone, methoxyhydroquinone, catechol, p-tert-butylcatechol, cresol, 2,6-di-tert-butyl-4-methylphenol (BHT), phenothiazine, and the like.

The composition of the present embodiment is preferably contained in a container filled with dry nitrogen gas having a dew point of −30° C. or lower in a gas phase portion. Thus, the contact of the compound (A) in the composition after the distillation process with water is prevented, and the increase of the compound (B) in the composition is suppressed. As a result, stability during storage and stability during use are improved.

As described above, since the composition of the present embodiment has excellent stability during storage and stability during use, it is not necessary to contain a large amount of a polymerization inhibitor which produces a colored component.

Therefore, it is possible to prevent the unsaturated compound produced by using the composition of the present invention from being colored by the coloring component caused by the polymerization inhibitor.

The composition of the present invention can be produced in high yield.

"Method for Producing Composition"

The method of producing the composition of the present embodiment is a method of producing the composition contained in a container.

The method of producing the composition of the present embodiment comprises a step of producing a mixture which contains compound (A) represented by general formula (1) and a compound (B) represented by general formula (2) and which contains more than 2.0 parts by mass of the compound (B) with respect to 100 parts by mass of the compound (A), and purifying the mixture by a distillation process at a reflux ratio of 2.0 to 4.0, a pressure of 1.0 to 10.0 kPa, and a distillation temperature of 90 to 140° C. The content of the compound (A) of the purified product (the composition) obtained by purification is preferably 95.0% by mass or more as described above, but is not limited thereto. Containing more than 2.0 parts by mass of the compound (B) with respect to 100 parts by mass of the compound (A) means to contain 2.0 parts by mass or more of the compound (B) with respect to 100 parts by mass of the compound (A).

(Step of Producing Mixture)

A method of producing a mixture which contains a compound (A) and a compound (B) and which contains more than 2.0 parts by mass of the compound (B) with respect to 100 parts by mass of the compound (A) can be arbitrarily selected, for example, a method of producing the compound (A) and producing the compound (B) simultaneously by using a conventionally known method of producing the compound (A) may be used.

Specifically, for example, the following methods and the like can be used. First, an unsaturated carboxylic acid aminoalkyl ester hydrochloride is synthesized by the reaction of an unsaturated carboxylic acid chloride with an amino alcohol hydrochloride. Next, an unsaturated carboxylic acid aminoalkyl ester hydrochloride is reacted with carbonyl chloride. Thus, the unsaturated carboxylic acid isocyanatoalkyl ester of the compound (A) is produced. At the same time, the compound (A) is reacted with an unsaturated carboxylic acid aminoalkyl ester hydrochloride to produce a compound (B), as a by-product, which is an impurity. However, it is not limited to this method.

The mixture of the compound (A) and the compound (B) thus obtained generally contains more than 2.0 parts by mass of the compound (B) with respect to 100 parts by mass of the compound (A).

The upper limit of the amount of the compound (B) contained in the mixture can be arbitrarily selected. For example, with respect to 100 parts by mass of the compound (A), the amount of the compound (B) is generally 10 parts by mass or less, preferably 8 parts by mass or less, and more preferably 6 parts by mass or less. However, the present invention is not limited to these examples.

The content of the compound (A) contained in the mixture can be arbitrarily selected, for example, the content of the compound (A) in the mixture is 55 to 85% by mass, may be 60 to 80% by mass, and is preferably 65 to 75% by mass. However, it is not limited to these.

(Purifying Step)

<Distillation Process>

In the present embodiment, the mixture of the compound (A) and the compound (B) thus obtained is purified by a distillation process at a reflux ratio (reflux/distillate) of 2.0 to 4.0, a pressure of 1.0 to 10.0 kPa, and a distillation temperature of 90 to 140° C. and the compound (A) is recovered as a low-boiling component. As a result, a purified product in which the content of the compound (B) with respect to 100 parts by mass of the compound (A) is 0.00002 to 2.0 parts by mass is obtained. Since compound (A) is usually a liquid, no solvent is required.

In the present embodiment, since the mixture is purified by the distillation process at the reflux ratio of 2.0 to 4.0, the compound (B) can be efficiently removed. When the reflux ratio is less than 2.0, since the physical properties of the compound (A) and the compound (B) are similar, the compound (B) cannot be sufficiently removed, and the content of the compound (B) with respect to 100 parts by mass of the compound (A) does not fall below 2.0 parts by mass. The reflux ratio is preferably 2.5 or more, more preferably 3.0 or more, in order to further reduce the content of the compound (B). When the reflux ratio is 4.0 or less, the purifying step can be carried out efficiently in a short time, the yield of the compound (A) in the composition can be sufficiently ensured, and the composition can be produced in a high yield. The reflux ratio is preferably 3.5 or less, more preferably 3.0 or less, in order to perform the purifying step more efficiently and further improve the yield of the compound (A).

In this embodiment, the distillation temperature in the purifying step is 90° C. to 140° C. When the distillation temperature is less than 90° C., the compound (A) and the compound (B) cannot be sufficiently separated, and the content of the compound (B) with respect to 100 parts by mass of the compound (A) does not become 2.0 parts by mass or less. Further, when the distillation temperature is 140° C. or lower, the compound (A) is not lost more than necessary, the yield of the compound (A) can be ensured, and the purifying step can be efficiently performed. In order to sufficiently remove compound (B) and to improve the yield of compound (A), the distillation temperature is preferably from 100° C. to 130° C., and more preferably from 110° C. to 120° C.

In this embodiment, the pressure at the time of distillation in the purifying step is 1.0 to 10.0 kPa, and preferably 1.0 to 6.0 kPa. When the pressure is 1.0 kPa or more, a flooding phenomenon is unlikely generated at a distillation temperature of 90 to 140° C., and a stable distillation state is easily maintained. When the pressure is 10.0 kPa or less, the compound (A) and the compound (B) are easily separated at a distillation temperature of 140° C. or lower, and the loss of the compound (A) due to increasing the distillation temperature is preferably suppressed.

When the distillation step is performed in the purifying step, a polymerization inhibitor may be added to the mixture before heating of the mixture is started. By adding the polymerization inhibitor to the mixture before starting the heating of the mixture, the mixture is prevented from Gelation by polymerization due to the temperature rise accompanying the distillation.

The polymerization inhibitor added to the mixture is partially removed by the distillation process. The polymerization inhibitor remaining in the composition after the distillation process prevents the composition from Gelation during storage and transportation of the composition and contributes to improvement of stability during storage of the composition. The polymerization inhibitor may optionally be added to the composition obtained after the distillation process.

Specific examples of the polymerization inhibitor include hydroquinone, methoxyhydroquinone, catechol, p-tert-butylcatechol, cresol, 2,6-di-tert-butyl-4-methylphenol (BHT), phenothiazine and the like.

In the purifying step, a vacuum breaking step is performed in which dry nitrogen gas having a dew point of −30° C. or lower is supplied into a distillation apparatus after the distillation process and the pressure in the distillation apparatus is returned to atmospheric pressure, and a filling step is performed in which the purified product in the distillation apparatus after the distillation process is stored in a container and the gas phase portion in the container is filled with dry nitrogen gas having a dew point of −30° C. or lower.

In the distillation apparatus at the time of the vacuum breaking step, the condition is such that the compound (B) is easily produced in the purified product. In the present embodiment, in the vacuum breaking step, dry nitrogen gas having a dew point of −30° C. or lower is supplied into the distillation apparatus after the distillation process to return the pressure in the distillation apparatus to atmospheric pressure, so that contact between the compound (A) in the purified product after the distillation process and moisture can be prevented. Further, in the present embodiment, the dry nitrogen gas having a dew point of −30° C. or lower is filled in the gas phase portion in the container in the filling step, so that contact between the compound (A) and moisture in the composition stored in the container can be prevented. Therefore, the formation or increase of the compound (B) in the composition can be prevented by performing the vacuum breaking step and the filling step. Therefore, the stability during storage and the stability during use are improved.

The dew point of the dry nitrogen gas supplied into the distillation apparatus in the vacuum breaking step and the dry nitrogen gas filled into the gas phase portion in the container in the filling step is −30° C. or lower and preferably −40° C. or lower in order to suppress the formation and increase of the compound (B) in the purified product. The dew point of the dry nitrogen gas used in the vacuum breaking step and the filling step is preferably −70° C. or higher because it is industrially readily available. It has been confirmed that even when the dew point of dry nitrogen gas is −70° C. or higher and less than −60° C., the same effect as that of dry nitrogen gas having a dew point of −60° C. or higher and −30° C. or lower can be obtained.

In the present embodiment, in order to more effectively prevent the increase of the compound (B) in the purified product, it is preferable that the purified product does not come into contact with a gas other than dry nitrogen gas having a dew point of −30° C. or lower in the step of feeding the purified product in the distillation apparatus after the distillation process into a container.

[Method for Producing Unsaturated Compound]

The method of producing an unsaturated compound according to the present embodiment includes a step of mixing the composition with a compound having active hydrogen and reacting the compound (A) contained in the composition with the compound having active hydrogen to obtain a reaction product (unsaturated compound).

In the present embodiment, the compound (A) contained in the composition used as the material of the unsaturated compound (reaction product) can be appropriately selected according to the structure of the unsaturated compound to be produced.

The active hydrogen in the compound having the active hydrogen is a hydrogen atom bonded to a nitrogen atom, an oxygen atom, a sulfur atom or the like, and exhibits high reactivity as compared with a hydrogen atom bonded to a carbon atom. The compound having active hydrogen is not particularly limited, and can be appropriately selected according to the structure of the unsaturated compound.

For example, when a compound having an active hydrogen-containing group, such as a hydroxyl group, a mercapto group, an amino group (including cyclic amines, amides and imides), and a carboxy group, is used as the active hydrogen-containing compound, the following reaction product (unsaturated compound) is obtained by the following reaction.

When a compound (A) contained in the composition is reacted with a compound having a hydroxyl group, the isocyanate group of the compound (A) reacts with the hydroxyl group to form an unsaturated urethane compound. In this embodiment, the unsaturated urethane compound means a compound containing an ethylenically unsaturated bond and a urethane bond in the molecule.

When a compound (A) contained in the composition is reacted with a compound having a mercapto group, the isocyanato group of the compound (A) is reacted with the mercapto group to form an unsaturated thiourethane compound. In this embodiment, the unsaturated thiourethane compound means a compound containing an ethylenically unsaturated bond and a thiourethane bond in the molecule.

When a compound (A) contained in the composition is reacted with a compound having an amino group, the isocyanate group of the compound (A) is reacted with the amino group to form an unsaturated urea compound. In this embodiment, the unsaturated urea compound means a compound containing an ethylenically unsaturated bond and a urea bond in the molecule.

When a compound (A) contained in the composition is reacted with a compound having a carboxy group, the isocyanato group of the compound (A) is reacted with the carboxy group to form an unsaturated amide compound. In this embodiment, the unsaturated amide compound means a compound containing an ethylenically unsaturated bond and an amide bond in the molecule.

The compound having a hydroxyl group can be arbitrarily selected, examples thereof include an aliphatic alcohol compound such as ethanol, n- or iso-propanol, butanol or its isomer, pentanol, hexanol, octanol, decanol, or the like; phenolic compounds such as phenol, cresol, p-nonylphenol, methyl salicylate; aliphatic polyols such as ethylene glycol, diethylene glycol, propylene glycol, tetramethylenediol, neopentyl glycol, 1,6-hexanediol, glycerol, trimethylolethane, trimethylolpropane, butanetriol, pentaerythritol, dipentaerythritol, tripentaerythritol, sorbitol, hexanetriol, triglycerol, polyethylene glycol, polypropylene glycol, ethylene oxide and propylene oxide copolymers, tris(2-hydroxyethyl) isocyanurate, cyclohexanediol, cyclohexanedimethanol, hydroxypropylhexanol, tricyclo [5, 2, 3, $0^{2,6}$] decanedimethanol, dicyclohexanediol, or the like; aromatic polyols such as dihydroxynaphthalene, dihydroxybenzene, bisphenol-A, bisphenol-F, pyrogallol, xylene glycol, bisphenol-A (2-hydroxyethyl ether); halogenated polyols such as dibromoneopentyl glycol; hydroxyl group-containing epoxy resin; phenoxy resin; polymeric polyols such as polyvinyl alcohol and (co) polymers of hydroxyethyl (meta) acrylate; terminal hydroxyl-containing reaction product obtained by reacting the above-mentioned polyol with an organic acid such as phthalic acid, pyromellitic acid, trimellitic acid, adipic acid, dimer acid or the like; addition reaction product of the above-mentioned polyols and alkylene oxide (ethylene oxide, propylene oxide, and the like); glucose derivatives such as hydroxyethyl cellulose and nitrocellulose; heterocycle-containing alcohols such as the carboxylic acid (formic acid, acetic acid, benzoic acid, or the like) orthoester of pentaerythritol; groups with both hydrogen atom and mercapto group, such as 2-mercaptoethanol; oxime-based compounds such as dimethyl ketone oxime, diethyl ketone oxime, methyl ethyl ketone oxime (MEK oxime) or the like; and the like.

Among the compounds having a hydroxyl group, polyol is preferable, and aliphatic polyol is more preferable.

The compound having the mercapto group can be optionally selected, and examples thereof include monothiols such as 1-butanethiol, 1-pentanethiol, 1-octanethiol, 1-dodecanethiol, n-octadecanethiol, α-toluenethiol, 2-benzimidazolethiol, 2-thiazoline-2-thiol, 2-methyl-2-propunchol, o-aminothiophenol, or the like; hexanedithiol, decanedithiol, 1,4-butanediol bisthiopropionate, 1,4-butanediol bisthioglycolate, ethylene glycol bisthioglycolate, ethylene glycol bisthioglycolate, ethylene glycol bisthiopropionate, trimethylolpropane trithioglycolate, trimethylolpropane tristhiopropionate, trimethylolpropane tristhiopropionate (3-mercaptobutylate), pentaerythritol tetrakis (2-mercaptopropionate), trimercaptopropionate tris(2-hydroxyethyl) isocyanurate, 1,4-dimethylmercaptobenzene, 2,4,6-trimercapto-s-triazine, 2-(N, N-dibutylamino)-4, 6-dimercapto-s-triazine, tetraethylene glycol bis (3-mercaptopropionate), trimethylolpropane tris(3-mercaptopropionate), tris(3-mercaptopropionyloxyethyl) isocyanurate, pentaerythritol tetrakis 3-mercaptopropionate, aliphatic polythiols, such as dipentaerythritol tetrakis (3-mercaptopropionate), 1,4-bis (3-mercaptobutyryloxy) butane (examples of specific products: "KarenzMT (registered trademark) PE1"), 1,3,5-tris(3-mercaptobutylate)-1,3,5-triazine-2,4,6 (1H, 3H, 5H)-trione (examples of specific products: "KarenzMT(registered trademark) NR1"), pentaerythritol tetrakis (3-mercaptobutylate) (examples of specific products: "KarenzMT (registered trademark) PE1"); and the like.

Among the compounds having a mercapto group, polythiol is preferable, and aliphatic polythiol is more preferable.

The compound having an amino group can be arbitrarily selected, but examples thereof include a monoamine such as butylamine, hexylamine or aniline; aliphatic polyamines such as diethylenetriamine, triethylenetetramine, 1,3- or 1,4-bisaminomethylcyclohexane, isophoronediamine, hexamethylenediamine, bis(4-aminocyclohexyl) methane or the like; aromatic polyamines such as m- or p-xylylenediamine, bis(4-aminophenyl) methane, 2,4- or 2,6-tolylenediamine or the like; glucosamines such as chitosan or the like; silicone compounds such as bis(3-aminopropyl) polydimethylsiloxane and bis(3-aminopropyl) polydiphenylsiloxane; heterocycle-containing compounds such as imidazole, E-caprolactam, phthalimide or the like; amides; imides; 2-[(3,5-dimethylpyrazolyl) carbonylamino] ethyl methacrylate (examples of specific products: "KarenzMOI-BP (registered trademark)"); 2-[(3,5-dimethylpyrazolyl) carbonylamino] ethyl acrylate; 3,5-dimethylpyrazole; and the like.

Among the compounds having an amino group, polyamines are preferable, and aliphatic polyamines are more preferable.

The compound having a carboxy group can be arbitrarily selected, but a monocarboxylic acid such as acetic acid, propionic acid, decanoic acid or the like; aliphatic and aromatic polycarboxylic acids such as succinic acid, adipic acid, phthalic acid, isophthalic acid, terephthalic acid, trimellitic acid, pyromellitic acid or the like; polymeric polycarboxylic acids such as polyamic acids, (co) polymers of acrylic acids or the like can be used.

Among the compounds having a carboxy group, polycarboxylic acids are preferable, and aliphatic and aromatic polycarboxylic acids are more preferable.

Further, as the compound having the active hydrogen, a halogen substitution such as a fluorine substitution or a chlorine substitution of the compound having the active hydrogen may be used. These may be used alone or in combination of two or more.

The active hydrogen-containing compound is preferably a polyol, a polythiol, a polyamine or a polycarboxylic acid in view of versatility, and is particularly preferably a polyol.

In the reaction of the compound (A) contained in the composition of the present embodiment with the compound having active hydrogen, the ratio of the compound (A) to the compound having active hydrogen is set in consideration of the ratio of isocyanate groups/active hydrogen.

The isocyanato group/active hydrogen ratio may be the same as that conventionally applied in the reaction of compound (A) with a compound having active hydrogen. The ratio of isocyanato group to active hydrogen varies depending on the kind of compound having active hydrogen.

The compound (A) contained in the composition of the present embodiment and the compound having active hydrogen may be reacted in the presence of a reaction catalyst. The reaction rate can be controlled by the addition amount of the reaction catalyst.

As the reaction catalyst, a known reaction catalyst can be used. Specific examples of reaction catalysts include dibutyltin dilaurate, copper naphthenate, cobalt naphthenate, zinc naphthenate, triethylamine, 1,4-diazabicyclo[2.2.2]octane, zirconium acetylacetonate, titanium diisopropoxybis (ethyl acetoacetate), mixtures of bismuth tris(2-ethylhexanoate) and 2-ethylhexanoic acid, and the like. These reaction catalysts may be used singly or in combination of two or more.

When the compound (A) contained in the composition of the present embodiment is reacted with a compound having active hydrogen, the reaction temperature is preferably −10 to 100° C., and more preferably 0 to 80° C.

When the compound (A) contained in the composition of the present embodiment is reacted with a compound having active hydrogen, a polymerization inhibitor may be added if necessary. As the polymerization inhibitor, a generally used one can be used, for example, a phenolic compound, a hydroquinone compound or the like can be used. Specific examples of polymerization inhibitors include hydroquinone, methoxyhydroquinone, catechol, p-tert-butylcatechol, cresol, 2,6-di-tert-butyl-4-methylphenol (BHT), and the like.

In addition, various substances such as known light stabilizers, ultraviolet absorbers, antioxidants, dye fillers, reactive diluents and the like may be added according to the purpose of the reaction.

The unsaturated compound (reaction product) is preferably at least one selected from the group consisting of unsaturated urethane compounds, unsaturated thiourethane compounds, unsaturated urea compounds and unsaturated amide compounds, and more preferably at least one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate) and 2-[(3,5-dimethylpyrazolyl) carbonylamino] ethyl acrylate.

The unsaturated compound thus obtained is preferably used as a material in various fields such as coating materials, adhesives, photoresists, contact lenses, solid electrolytes, solidification of bioactive substances or the like.

The composition of the present embodiment is a composition which contains a compound (A) represented by general formula (1) and a compound (B) represented by general formula (2) and which contains 0.00002 to 2.0 parts by mass of the compound (B) with respect to 100 parts by mass of the compound (A). Therefore, it is excellent in stability during storage and stability during use. Further, it is not necessary to contain a large amount of the polymerization inhibitor which forms the colored component. Therefore, it is possible to prevent the unsaturated compound produced by using the composition of the present embodiment from being colored by the coloring component caused by the polymerization inhibitor.

Further, since the composition of the present embodiment contains 0.00002 parts by mass or more of the compound (B) with respect to 100 parts by mass of the compound (A), the composition can be produced in a high yield.

In the method of producing the composition of the present embodiment, a mixture, which contains more than 2.0 parts by mass of the compound (B) with respect to 100 parts by mass of the compound (A), is purified by a distillation process at a reflux ratio of 2.0 to 4.0, a pressure of 1.0 to 10.0 kPa, and a distillation temperature of 90 to 140° C. to obtain a purified product containing 0.00002 to 2.0 parts by mass of the compound (B) with respect to 100 parts by mass of the compound (A). Therefore, according to the method of producing the composition of the present embodiment, the composition of the present embodiment can be produced in a high yield in which the compound (B) that affects the stability during storage and affects the stability during use is sufficiently removed from the mixture.

Further, in the method of producing the composition of the present embodiment, in the purifying step, a vacuum breaking step and a filling step are carried out, and in the vacuum breaking step, dry nitrogen gas having a dew point of −30° C. or lower is supplied into the distillation apparatus after the distillation process and the pressure in the distillation apparatus is returned to atmospheric pressure; and in the filling step, the purified product in the distillation apparatus after the distillation process is stored in a container and the gas phase portion in the container is filled with dry nitrogen gas having a dew point of −30° C. or lower. Therefore, the compound (A) in the purified product after distillation process is unlikely brought into contact with water, and the compound (B) is unlikely increased in the purified product. Therefore, according to the method of producing the composition of the present embodiment, a composition having good stability during storage and stability during use can be obtained.

The method of producing the unsaturated compound of the present embodiment includes a step of mixing the composition of the present invention with a compound having active hydrogen and reacting the compound (A) contained in the composition with the compound having active hydrogen to obtain a reaction product. In the method of producing the unsaturated compound according to the present embodiment, the composition used as the material contains 0.00002 to 2.0 parts by mass of the compound (B) with respect to 100 parts by mass of the compound (A). Therefore, rapid increase in viscosity or gelation of the reaction product is unlikely to occur during production, and excellent productivity is obtained.

EXAMPLES

Hereinafter, this embodiment will be described in detail with reference to Examples and Comparative Examples. It should be noted that the following embodiments are intended to facilitate understanding of the contents of the present embodiment, and the present embodiment is not limited only to these embodiments.

Mixture 1 and Mixture 2 were prepared by the following methods.

<Mixture 1> (Synthesis of MOI)

In a 500 ml four-necked flask equipped with a stirrer, condenser, thermometer and inner tube, 250 ml of toluene and 25 g (0.41 mol) of 2-aminoethanol were added, heated to 90° C. and supplied with about 20 g of hydrogen chloride gas. Then, 44 g (0.42 mol) of methacrylic acid chloride was added dropwise, and the mixture was heated at 90° C. for 1 hour. Thereafter, 80 g (0.81 mol) of phosgene was supplied. 0.4 g of phenothiazine and 0.4 g of 2,6-bis-tert-butylhydroxytoluene were then added, and dissolved phosgene and toluene were removed.

By the above process, Mixture 1 containing the main product (the compound (A)) of 2-methacryloyloxyethyl isocyanate (MOI) 45 g (0.29 mol) (71% yield) and the by-product (the compound (B)) of N, N'-bis(2-methacryloyloxyethyl) urea (56375 ppm by mass) was obtained.

<Mixture 2> (Synthesis of AOI)

In a 500 mL four-necked flask equipped with a stirrer, condenser, thermometer and inner tube, 250 mL of toluene and 25 g (0.41 mol) of 2-aminoethanol were added, heated to 90° C. and supplied with about 20 g of hydrogen chloride gas. Then 56 g (0.44 mol) of 3-chloropropionic acid chloride was added dropwise over 90 minutes and heated at 90° C. for 1 hour. Thereafter, 80 g (0.81 mol) of phosgene was supplied. Dissolved phosgene was then removed by nitrogen gas bubbling. Subsequently, 0.4 g of phenothiazine and 0.4 g of 2,6-bis-t-butylhydroxytoluene were added, and 50 g of triethylamine (0.49 mol) was supplied, and the mixture was heated and stirred at 50° C. for 6 hours. Thereafter, the mixture was cooled to room temperature, the formed hydrochloride salt was filtered, and toluene was distilled off.

By the above process, Mixture 2 containing the main product (the compound (A)) of 2-acryloyloxyethyl isocyanate (AOI) 55 g (0.35 mol) (87% yield) and the by-product (the compound (B)) of N, N'-bis(2-Acryloyloxyethyl) urea (48657 ppm by mass) was obtained.

Examples 1 to 6 and Comparative Examples 1 to 8> (MOI)

50 g of Mixture 1 was distilled under the conditions shown in Tables 1 and 2 (reflux ratio (reflux/distillate), distillation temperature, distillation pressure). The liquid compositions of Examples 1 to 6 and Comparative Examples 1 to 8 contained in a container were obtained by carrying out a vacuum breaking step in which the gas shown in Tables 1 and 2 was supplied into the distillation apparatus after the distillation process to return the pressure in the distillation apparatus to atmospheric pressure, and a filling step in which the purified product in the distillation apparatus after the distillation process was contained in a transparent glass container and the gas phase portion in the container was filled with the gas shown in Tables 1 and 2.

<Examples 7 to 12 and Comparative Examples 9 to 16> (AOI)

50 g of mixture 2 was distilled under the conditions shown in Tables 3 and 4 (reflux ratio (reflux/distillate), distillation temperature, distillation pressure). Thereafter, in the same manner as described above, a vacuum breaking step of supplying the gas shown in Tables 3 and 4 into the distillation apparatus after the distillation process and returning the pressure in the distillation apparatus to the atmospheric pressure was carried out, and the filling step of storing the purified product in the distillation apparatus after the distillation process in a transparent glass container and filling the gas phase portion in the container with the gas shown in Tables 3 and 4 was carried out to obtain the liquid compositions of Examples 7 to 12 and Comparative Examples 9 to 16 stored in the container.

TABLE 1

| Example | 1 | 2 | 3 |
|---|---|---|---|
| Distillation temperature(° C.) | 110 | 115 | 90 |
| Distillation pressure (kPa) | 2.0 | 2.5 | 1.0 |
| Reflux ratio | 3.5 | 3.0 | 3.5 |
| Gas supplied in the vacuum breaking step | Dried nitrogen gas (Dew point: −60° C.) | Dried nitrogen gas (Dew point: −30° C.) | Dried nitrogen gas (Dew point: −40° C.) |
| Gas filled in the filling step | Dried nitrogen gas (Dew point: −50° C.) | Dried nitrogen gas (Dew point: −50° C.) | Dried nitrogen gas (Dew point: −30° C.) |
| Compound A content (% by mass) | 98.0 | 98.5 | 98.7 |
| Compound B Content ($\times 10^{-4}$ parts by mass) | 154 | 213 | 759 |
| Yield (%) | 85 | 87 | 90 |
| Viscosity (mPa · sec) | 1.5 | 1.7 | 1.6 |
| Appearance | No change | No change | No change |

| Example | 4 | 5 | 6 |
|---|---|---|---|
| Distillation temperature(° C.) | 100 | 135 | 130 |
| Distillation pressure (kPa) | 1.5 | 6.0 | 6.0 |
| Reflux ratio | 2.5 | 2.0 | 4.0 |
| Gas supplied in the vacuum breaking step | Dried nitrogen gas (Dew point: −35° C.) | Dried nitrogen gas (Dew point: −40° C.) | Dried nitrogen gas (Dew point: −30° C.) |
| Gas filled in the filling step | Dried nitrogen gas (Dew point: −50° C.) | Dried nitrogen gas (Dew point: −50° C.) | Dried nitrogen gas (Dew point: −40° C.) |
| Compound A content (% by mass) | 98.2 | 99.2 | 99.4 |
| Compound B Content ($\times 10^{-4}$ parts by mass) | 489 | 356 | 623 |
| Yield (%) | 88 | 84 | 78 |
| Viscosity (mPa · sec) | 1.7 | 1.7 | 1.6 |
| Appearance | No change | No change | No change |

TABLE 2

| Comparative Example | 1 | 2 | 3 | 4 |
|---|---|---|---|---|
| Distillation temperature(° C.) | 90 | 110 | 135 | 110 |
| Distillation pressure (kPa) | 1.0 | 2.0 | 6.5 | 2.0 |
| Reflux ratio | 1.0 | 0.2 | 1.5 | 0.5 |
| Gas supplied in the vacuum breaking step | Dried nitrogen gas (Dew point: −40° C.) | Dried nitrogen gas (Dew point: −30° C.) | Dried nitrogen gas (Dew point: −20° C.) | Dried nitrogen gas (Dew point: −30° C.) |
| Gas filled in the filling step | Dried nitrogen gas (Dew point: −30° C.) | Dried nitrogen gas (Dew point: −50° C.) | Dried nitrogen gas (Dew point: −40° C.) | Dried nitrogen gas (Dew point: −20° C.) |
| Compound A content (% by mass) | 97.5 | 97.0 | 97.8 | 96.3 |
| Compound B Content ($\times 10^{-4}$ parts by mass) | 25317 | 23007 | 24006 | 28648 |
| Yield (%) | 93 | 90 | 85 | 88 |
| Viscosity (mPa · sec) | Not measurable | Not measurable | Not measurable | Not measurable |
| Appearance | Syrup-like | Solid | Syrup-like | Solid |

TABLE 2-continued

| Comparative Example | 5 | 6 | 7 | 8 |
|---|---|---|---|---|
| Distillation temperature(° C.) | 90 | 100 | 135 | 130 |
| Distillation pressure (kPa) | 1.0 | 1.5 | 6.0 | 6.0 |
| Reflux ratio | 3.5 | 2.5 | 2.0 | 4.5 |
| Gas supplied in the vacuum breaking step | Air | Dried nitrogen gas (Dew point: −40° C.) | Dried nitrogen gas (Dew point: −50° C.) | Air |
| Gas filled in the filling step | Dried nitrogen gas (Dew point: −50° C.) | Air | Air | Dried nitrogen gas (Dew point: −30° C.) |
| Compound A content (% by mass) | 98.2 | 97.7 | 98.7 | 98.9 |
| Compound B Content (×10$^{-4}$ parts by mass) | 32546 | 58975 | 35687 | 66458 |
| Yield (%) | 90 | 88 | 84 | 78 |
| Viscosity (mPa · sec) | Not measurable | Not measurable | Not measurable | Not measurable |
| Appearance | Syrup-like | Solid | Syrup-like | Solid |

TABLE 3

| Example | 7 | 8 | 9 |
|---|---|---|---|
| Distillation temperature(° C.) | 90 | 120 | 130 |
| Distillation pressure (kPa) | 1.5 | 3.5 | 6.5 |
| Reflux ratio | 3.5 | 2.0 | 3.5 |
| Gas supplied in the vacuum breaking step | Dried nitrogen gas (Dew point: −60° C.) | Dried nitrogen gas (Dew point: −60° C.) | Dried nitrogen gas (Dew point: −40° C.) |
| Gas filled in the filling step | Dried nitrogen gas (Dew point: −40° C.) | Dried nitrogen gas (Dew point: −30° C.) | Dried nitrogen gas (Dew point: −40° C.) |
| Compound A content (% by mass) | 98.6 | 98.5 | 99.4 |
| Compound B Content (×10$^{-4}$ parts by mass) | 358 | 487 | 523 |
| Yield (%) | 88 | 82 | 80 |
| Viscosity(mPa · sec) | 1.6 | 1.8 | 1.6 |
| Appearance | No change | No change | No change |

| Example | 10 | 11 | 12 |
|---|---|---|---|
| Distillation temperature(° C.) | 110 | 115 | 125 |
| Distillation pressure (kPa) | 2.5 | 3.0 | 4.5 |
| Reflux ratio | 2.5 | 2.0 | 4.0 |
| Gas supplied in the vacuum breaking step | Dried nitrogen gas (Dew point: −30° C.) | Dried nitrogen gas (Dew point: −50° C) | Dried nitrogen gas (Dew point: −30° C.) |
| Gas filled in the filling step | Dried nitrogen gas (Dew point: −40° C.) | Dried nitrogen gas (Dew point: −60° C.) | Dried nitrogen gas (Dew point: −40° C.) |
| Compound A content (% by mass) | 98.2 | 99.2 | 99.6 |
| Compound B Content (×10$^{-4}$ parts by mass) | 654 | 338 | 597 |
| Yield (%) | 86 | 84 | 72 |
| Viscosity(mPa · sec) | 1.7 | 1.7 | 1.6 |
| Appearance | No change | No change | No change |

TABLE 4

| Comparative Example | 9 | 10 | 11 | 12 |
|---|---|---|---|---|
| Distillation temperature(° C.) | 90 | 110 | 130 | 110 |
| Distillation pressure (kPa) | 1.5 | 2.5 | 6.5 | 2.5 |
| Reflux ratio | 1 | 0.2 | 1.5 | 0.5 |
| Gas supplied in the vacuum breaking step | Dried nitrogen gas (Dew point: −50° C.) | Dried nitrogen gas (Dew point: −60° C.) | Dried nitrogen gas (Dew point: −30° C.) | Dried nitrogen gas (Dew point: −40° C.) |
| Gas filled in the filling step | Dried nitrogen gas (Dew point: −60° C.) | Dried nitrogen gas (Dew point: −40° C.) | Dried nitrogen gas (Dew point: −50° C) | Dried nitrogen gas (Dew point: −50° C.) |
| Compound A content (% by mass) | 97.5 | 97.0 | 97.8 | 96.3 |
| Compound B Content (×10$^{-4}$ parts by mass) | 26578 | 22897 | 28674 | 33265 |

TABLE 4-continued

| | | | | |
|---|---|---|---|---|
| Yield (%) | 91 | 90 | 81 | 88 |
| Viscosity (mPa · sec) | Not measurable | Not measurable | Not measurable | Not measurable |
| Appearance | Syrup-like | Solid | Syrup-like | Solid |
| Comparative Example | 13 | 14 | 15 | 16 |
| Distillation temperature(° C.) | 130 | 110 | 115 | 125 |
| Distillation pressure (kPa) | 6.5 | 2.5 | 3.0 | 4.5 |
| Reflux ratio | 3.5 | 2.5 | 2.0 | 4.5 |
| Gas supplied in the vacuum breaking step | Air | Dried nitrogen gas (Dew point: −40° C.) | Dried nitrogen gas (Dew point: −50° C.) | Air |
| Gas filled in the filling step | Dried nitrogen gas (Dew point: −60° C.) | Air | Air | Dried nitrogen gas (Dew point: −30° C.) |
| Compound A content (% by mass) | 99.4 | 98.2 | 99.2 | 99.6 |
| Compound B Content (×10$^{-4}$ parts by mass) | 35687 | 43652 | 37885 | 56782 |
| Yield (%) | 80 | 86 | 84 | 72 |
| Viscosity (mPa · sec) | Not measurable | Not measurable | Not measurable | Not measurable |
| Appearance | Syrup-like | Solid | Syrup-like | Solid |

Next, regarding the compositions of Examples 1 to 12 and Comparative Examples 1 to 16, the compound (A) and the compound (B) in each the composition were determined quantitatively by the following method, and the content (% by mass) of the compound (A) and the content (×10$^{-4}$ parts by mass) of the compound (B) with respect to 100 parts by mass of the compound (A) in each the composition were determined. The results are shown in Tables 1 to 4.

<Quantification of Compound (A) and Compound (B)>

The composition was subjected to gas chromatography (GC) analysis by an internal standard method under the following conditions.

Column: DB-1, Inlet Temperature: 300° C., Detection Temperature: 300° C.

Column temperature: 50° C. to 300° C. at 10° C./min

Column flow rate: 1.4 ml/min

Split ratio: 1/50

Detector: FID

The yields (distillation yield) of the compositions (crude products) of Examples 1 to 12 and Comparative Examples 1 to 16 were determined by the following formula. The results are shown in Tables 1 to 4.

Yield=(the composition Mass/Theoretical Yield)×100(%)

"Appearance Evaluation"

In Examples 1 to 12 and Comparative Examples 1 to 16, 100 g of the liquid compositions immediately after the distillation process were stored in a transparent glass container in a sealed state at 25° C. for 30 days under a nitrogen gas atmosphere, and the appearance after storage was evaluated by the following method.

The transparent glass container containing the composition was tilted several times at an angle of about 45 degrees and evaluated visually using the following criteria. The results are shown in Tables 1 to 4.

"Criteria"

No change: flowing in less than 30 seconds after tilting the glass container

Syrup-like: flowing down in 30 seconds or more and less than 180 seconds after tilting a glass container Solid: not flowing in more than 180 seconds after tilting the glass container "Method of Measuring Viscosity"

The viscosities of the compositions of Examples 1 to 12 and Comparative Examples 1 to 16 stored at 25° C. for 30 days in a sealed state were determined in accordance with JIS-Z 8803: 2011 by the following method. The results are shown in Tables 1 to 4.

The kinematic viscosity (cm$^3$/sec) of each composition at 25° C. was measured using an Uberode viscometer. In Examples 1 to 6 and Comparative Examples 1 to 8, the measured kinematic viscosity was multiplied by the density of the following KarenzMOI (registered trademark) (manufactured by Showa Denko) to calculate the viscosity (mPa·sec). In Examples 7 to 12 and Comparative Examples 9 to 16, the viscosity was calculated by multiplying the measured value of the kinematic viscosity by the density of the KarenzAOI (registered trademark) (manufactured by Showa Denko) shown below (mPa·sec).

(Density of the KarenzMOI (registered trademark)) 1.096 g/cm$^3$ (25° C.)

(Density of KarenzAOI (registered trademark)) 1.133 g/cm$^3$ (25° C.)

As shown in Tables 1 to 4, the compositions of Examples 1 to 12, which contain 0.00002 to 2.0 parts by mass of Compound (B) with respect to 100 parts by mass of Compound (A), had a sufficiently low viscosity after storage at 25° C. for 30 days, and the appearance evaluation were "No change".

On the other hand, in the compositions of Comparative Examples 1 to 16, which contain more than 2.0 parts by mass of the compound (B) with respect to 100 parts by mass of Compound (A), the viscosity which became too high by storing at 25° C. for 30 days, and the viscosity could not be measured. In the compositions of Comparative Examples 1 to 16, the appearance evaluations were "syrup-like" or "solid".

(Unsaturated Compound)

<Example 13> (Reaction Product of (Poly)ol with MOI)

In a 500 ml four-necked flask equipped with a stirrer, reflux condenser and thermometer, 165 g of polyethylene glycol (number-average molecular weight 660) and 77.5 g of the composition of Example 1 (The compound (A) is MOI.) were charged and reacted at 80° C. for 5 hours to synthesize an unsaturated urethane compound 1.

<Comparative Example 17> (Reaction Product of (Poly)ol with MOI)

An unsaturated urethane compound 2 was synthesized in the same manner as in Example 13 except that the composition of Comparative Example 1 (The compound (A) is MOI.) was used in place of the composition of Example 1.

<Comparative Example 18> (Reaction Product of (Poly)ol with MOI)

An unsaturated urethane compound 3 was synthesized in the same manner as in Example 13 except that the composition of Comparative Example 7 (The compound (A) is MOI.) was used in place of the composition of Example 1.

<Example 14> (Reaction Product of (Poly)ol with AOI)

In a 500 ml four-necked flask equipped with a stirrer, reflux condenser and thermometer, 165 g of polyethylene glycol (number-average molecular weight 660) and 70.5 g of the composition of Example 9 (The compound (A) is AOI.) were charged and reacted at 80° C. for 5 hours to synthesize an unsaturated urethane compound 4.

<Comparative Example 19> (Reaction Product of (Poly)ol with AOI)

An unsaturated urethane compound 5 was synthesized in the same manner as in Example 14 except that the composition of Comparative Example 12 (The compound (A) is AOI.) was used in place of the composition of Example 9.

<Comparative Example 20> (Reaction Product of (Poly)ol with AOI)

An unsaturated urethane compound 6 was synthesized in the same manner as in Example 14 except that the composition of Comparative Example 16 (The compound (A) is AOI.) was used in place of the composition of Example 9.

Viscosities of the reaction liquids containing the unsaturated urethane compounds 1 to 6, obtained in Examples 13 and 14 and Comparative Examples 17 to 20, were measured in accordance with JIS-Z 8803: 2011 at 25° C. using a tuning fork type vibrating viscometer (SV type viscometer manufactured by A & D Co., Ltd. (SV −10 Type)). The results are shown in Tables 5 and 6.

As shown in Table 5, in Example 13 in which the unsaturated urethane compounds were prepared by using the composition containing 0.00002 to 2.0 parts by mass of the compound (B) with respect to 100 parts by mass of the compound (A), the unsaturated urethane compound 1 having an appropriate viscosity was obtained, and the unsaturated urethane compound could be produced without problem.

On the other hand, in Comparative Examples 17 and 18 in which the unsaturated urethane compounds were prepared by using the composition containing more than 2.0 parts by mass of Compound (B) with respect to 100 parts by mass of Compound (A), the unsaturated urethane compounds 2 and 3 were gelatinized during the preparation of the unsaturated urethane compounds 2 and 3, although there was no problem in handling in the raw material stage.

As shown in Table 6, in Example 14 in which the unsaturated urethane compounds were prepared by using a composition containing 0.00002 to 2.0 parts by mass of Compound (B) with respect to 100 parts by mass of Compound (A), the unsaturated urethane compound 4 having an appropriate viscosity was obtained, and the unsaturated urethane compound could be produced without any problem.

On the other hand, in Comparative Examples 19 and 20 in which the unsaturated urethane compounds were prepared by using the composition containing more than 2.0 parts by mass of Compound (B) with respect to 100 parts by mass of Compound (A), the viscosity of the unsaturated urethane compounds 5 and 6 was high, and a part of them gelled during the preparation.

<Example 15> (Reaction Product of (Poly)amine with MOI)

A 500 ml four-necked flask equipped with a stirrer, reflux condenser and thermometer was charged with 66.4 g of (2-[(3,5-Dimethylpyrazolyl)carbonylamino]ethyl methacrylate) (KarenzMOI-BP (registered trademark) manufactured by Showa Denko) and 77.4 g of 3,5-dimethylpyrazole, and 122.6 g of the composition of Example 2 (The compound (A) is MOL) was supplied while the temperature was

TABLE 5

| | Unsaturated Urethane Compound | Composition | Compound B Content in Composition ($\times 10^{-4}$ parts by mass) | Viscosity (mPa · sec) |
|---|---|---|---|---|
| Example 13 | 1 | Example 1 | 154 | 0.16 |
| Comparative Example 17 | 2 | Comparative Example 1 | 25317 | gelation |
| Comparative Example 18 | 3 | Comparative Example 7 | 35687 | gelation |

TABLE 6

| | Unsaturated Urethane Compound | Composition | Compound B Content in Composition ($\times 10^{-4}$ parts by mass) | Viscosity (mPa · sec) |
|---|---|---|---|---|
| Example 14 | 4 | Example 9 | 523 | 0.16 |
| Comparative Example 19 | 5 | Comparative Example 12 | 33265 | Gelation |
| Comparative Example 20 | 6 | Comparative Example 16 | 56782 | Gelation | maintained at 35° C., and then reacted for 2 hours to synthesize unsaturated urea compound 1.

<Comparative Example 21> (Reaction Product of (Poly)amine with MOI)

The unsaturated urea compound 2 was synthesized in the same manner as in Example 15 except that the composition of Comparative Example 2 (The compound (A) is MOI.) was used in place of the composition of Example 2.

<Comparative Example 22> (Reaction Product of (Poly)amine with MOI)

The unsaturated urea compound 3 was synthesized in the same manner as in Example 15 except that the composition of Comparative Example 5 (The compound (A) is MOI.) was used in place of the composition of Example 2.

<Example 16> (Reaction Product of (Poly)amine with AOI)

In a 1000 ml four-necked flask equipped with a stirrer, reflux condenser and thermometer, 115.9 g of 3,5-dimethylpyrazole and 155.0 g of 2-acetoxy-1-methoxypropane were charged, 174.0 g of the composition of Example 8 (The compound (A) is AOI.) was fed while maintaining the temperature at 15° C., and then reacted for 30 minutes. Subsequently, 320.0 g of n-hexane was added and cooled to 0° C. to crystallize an unsaturated urea compound 4. The obtained crystals were recovered by filtration, washed with n-hexane, and dried under reduced pressure to isolate the unsaturated urea compound 4.

<Comparative Example 23> (Reaction Product of (Poly)amine with AOI.)

An unsaturated urea compound 5 was synthesized in the same manner as in Example 16 except that the composition of Comparative Example 10 (The compound (A) is AOI.) was used in place of the composition of Example 8.

<Comparative Example 24> (Reaction Product of (Poly)amine with AOI)

An unsaturated urea compound 6 was synthesized in the same manner as in Example 16 except that the composition of Comparative Example 15 (The compound (A) is AOI.) was used in place of the composition of Example 8.

Viscosities of the reaction liquids containing the unsaturated urea compounds 1 to 6 obtained in Examples 15 and 16 and Comparative Examples 21 to 24 were measured in accordance with JIS-Z 8803: 2011 at 25° C. using a tuning fork type vibration type viscometer (SV type viscometer manufactured by A & D Co., Ltd. (SV -10 Type)). The results are shown in Tables 7 and 8.

TABLE 7

| | Unsaturated Urea Compound | Composition | Compound B Content in Composition ($\times 10^{-4}$ parts by mass) | Viscosity (mPa · sec) |
|---|---|---|---|---|
| Example 15 | 1 | Example 2 | 213 | 0.18 |
| Comparative Example 21 | 2 | Comparative Example 2 | 23007 | Gelation |
| Comparative Example 22 | 3 | Comparative Example 5 | 32546 | Gelation |

TABLE 8

| | Unsaturated Urea Compound | Composition | Compound B Content in Composition ($\times 10^{-4}$) Weight Part | Viscosity (mPa · sec) |
|---|---|---|---|---|
| Example 16 | 4 | Example 8 | 487 | 0.22 |
| Comparative Example 23 | 5 | Comparative Example 10 | 22897 | Gelation |
| Comparative Example 24 | 6 | Comparative Example 15 | 37885 | Gelation |

As shown in Table 7, in Example 15 in which unsaturated urea compounds were prepared by using the composition containing 0.00002 to 2.0 parts by mass of Compound (B) with respect to 100 parts by mass of Compound (A), the unsaturated urea compound 1 having an appropriate viscosity was obtained, and the unsaturated urea compound was successfully prepared.

On the other hand, in Comparative Examples 21 and 22 in which unsaturated urea compounds were prepared by using the composition containing more than 2.0 parts by mass of Compound (B) with respect to 100 parts by mass of Compound (A), the unsaturated urea compounds 2 and 3 were gelled during the preparation, although there was no problem in handling at the stage of raw material.

As shown in Table 8, in Example 16 in which unsaturated urea compounds were prepared by using a composition containing 0.00002 to 2.0 parts by mass of Compound (B) with respect to 100 parts by mass of Compound (A), the unsaturated urea compound 4 having a proper viscosity was obtained, and the unsaturated urea compound was successfully prepared.

On the other hand, in Comparative Examples 23 and 24 in which unsaturated urea compounds were prepared by using the composition containing more than 2.0 parts by mass of Compound (B) with respect to 100 parts by mass of Compound (A), the unsaturated urea compounds 5 and 6 were gelled during the preparation, although there was no problem in handling at the stage of raw material.

<Example 17> (Reaction Product of (Poly)carboxylic Acid with MOI)

In a 500 ml four-necked flask equipped with a stirrer, reflux condenser and thermometer, 177.3 g of decanoic acid, 156.5 g of the composition of Example 3 (The compound (A) is MOI.) and 0.8 g of dibutyltin dilaurate were charged and reacted at 80° C. for 12 hours to synthesize an unsaturated amide compound 1.

<Comparative Example 25> (Reaction Product of (Poly)carboxylic Acid with MOI)

An unsaturated amide compound 2 was synthesized in the same manner as in Example 17 except that the composition of Comparative Example 3 (The compound (A) is MOI.) was used in place of the composition of Example 3.

<Comparative Example 26> (Reaction Product of (Poly)carboxylic Acid with MOI)

The unsaturated amide compound 3 was synthesized in the same manner as in Example 17 except that the composition of Comparative Example 8 (The compound (A) is MOI.) was used in place of the composition of Example 3.

<Example 18> (Reaction Product of (Poly)carboxylic Acid with AOI)

In a 500 ml four-necked flask equipped with a stirrer, reflux condenser and thermometer, 177.3 g of decanoic acid, 142.4 g of the composition of Example 7 (The compound (A) is AOI.) and 0.8 g of dibutyltin dilaurate were charged and reacted at 80° C. for 12 hours to synthesize an unsaturated amide compound 4.

<Comparative Example 27> (Reaction Product of (Poly)carboxylic Acid with AOI)

An unsaturated amide compound 5 was synthesized in the same manner as in Example 18 except that the composition of Comparative Example 11 (The compound (A) is AOI.) was used in place of the composition of Example 7.

<Comparative Example 28> (Reaction Product of (Poly)carboxylic Acid with AOI)

An unsaturated amide compound 6 was synthesized in the same manner as in Example 18 except that the composition of Comparative Example 14 (The compound (A) is AOI.) was used in place of the composition of Example 7.

Viscosities of the reaction liquids containing the unsaturated amide compounds 1 to 6 obtained in Examples 17 and 18 and Comparative Examples 25 to 28 were measured in accordance with JI-Z 8803: 2011 at 25° C. using a tuning fork type vibrating viscometer (SV type viscometer manufactured by A & D Co., Ltd. (SV-10 Type)).

TABLE 9

| | Unsaturated Amide Compound | Composition | Compound B Content in Composition ($\times 10^{-4}$ parts by mass) | Viscosity (mPa · sec) |
|---|---|---|---|---|
| Example 17 | 1 | Example 3 | 759 | 0.77 |
| Comparative Example 25 | 2 | Comparative Example 3 | 24006 | Gelation |
| Comparative Example 26 | 3 | Comparative Example 8 | 66458 | Gelation |

TABLE 10

| | Unsaturated Amide Compound | Composition | Compound B Content in Composition ($\times 10^{-4}$ parts by mass) | Viscosity (mPa · sec) |
|---|---|---|---|---|
| Example 18 | 4 | Example 7 | 358 | 0.22 |
| Comparative Example 27 | 5 | Comparative Example 11 | 28674 | Gelation |
| Comparative Example 28 | 6 | Comparative Example 14 | 43652 | Gelation |

As shown in Table 9, in Example 17 in which unsaturated amide compounds were prepared by using the composition containing 0.00002 to 2.0 parts by mass of Compound (B) with respect to 100 parts by mass of Compound (A), the unsaturated amide compound 1 having a proper viscosity was obtained, and the unsaturated amide compound could be prepared without any problem.

On the other hand, in Comparative Examples 25 and 26 in which unsaturated amide compounds were prepared by using the composition containing more than 2.0 parts by mass of Compound (B) with respect to 100 parts by mass of Compound (A), although there was no problem in handling in the stage of raw material, they gelled during the preparation of the unsaturated amide compounds 2 and 3.

As shown in Table 10, in Example 18 in which unsaturated amide compounds were prepared by using the composition containing 0.00002 to 2.0 parts by mass of Compound (B) with respect to 100 parts by mass of Compound (A), the unsaturated amide compound 4 having a proper viscosity was obtained, and the unsaturated amide compound was successfully prepared.

On the other hand, in Comparative Examples 27 and 28 in which unsaturated amide compounds were prepared by using the composition containing more than 2.0 parts by mass of Compound (B) with respect to 100 parts by mass of Compound (A), although there was no problem in handling in the stage of raw material, they gelled during the preparation of the unsaturated amide compounds 5 and 6.

<Example 19> (Reaction Product of (Poly)thiol with MOI)

In a 500 ml four-necked flask equipped with a stirrer, reflux condenser and thermometer, 177.3 g of 1-octanethiol and 184.3 g of the composition of Example 4 (The compound (A) is MOI.) were charged and reacted at 80° C. for 24 hours to synthesize an unsaturated thiourethane compound 1.

<Comparative Example 29> (Reaction Product of (Poly)thiol with MOI)

An unsaturated thiourethane compound 2 was synthesized in the same manner as in Example 19 except that the composition of Comparative Example 4 (The compound (A) is MOI.) was used in place of the composition of Example 4.

<Comparative Example 30> (Reaction of (Poly)thiol with MOI)

An unsaturated thiourethane compound 3 was synthesized in the same manner as in Example 19 except that the composition of Comparative Example 6 (The compound (A) is MOI.) was used in place of the composition of Example 4.

<Example 20> (Reaction Product of (Poly)thiol with AOI)

In a 500 ml four-necked flask equipped with a stirrer, reflux condenser and thermometer, 177.3 g of 1-octanethiol and 167.7 g of the composition of Example 12 (The compound (A) is AOI.) were charged and reacted at 80° C. for 24 hours to synthesize an unsaturated thiourethane compound 4.

<Comparative Example 31> (Reaction Product of (Poly)thiol with AOI)

An unsaturated thiourethane compound 5 was synthesized in the same manner as Example 20 except that the composition of Comparative Example 9 (The compound (A) is AOI.) was used in place of the composition of Example 12.

<Comparative Example 32> (Reaction Product of (Poly)thiol with AOI)

An unsaturated thiourethane compound 6 was synthesized in the same manner as in Example 20 except that the composition of Comparative Example 13 (The compound (A) is AOI.) was used in place of the composition of Example 12.

Viscosities of the reaction liquids containing the unsaturated thiourethane compounds 1 to 6 obtained in Examples 19 and 20 and Comparative Examples 29 to 32 were measured in accordance with JIS-Z 8803: 2011 at 25° C. using a tuning fork type vibrating viscometer (SV type viscometer manufactured by A & D Co., Ltd. (SV −10 Type)). The results are shown in Tables 11 and 12.

TABLE 11

| | Unsaturated thiourethane compound | Composition | Compound B Content in Composition ($\times 10^{-4}$ parts by mass) | Viscosity (mPa · sec) |
|---|---|---|---|---|
| Example 19 | 1 | Example 4 | 489 | 0.87 |
| Comparative Example 29 | 2 | Comparative Example 4 | 28648 | Gelation |
| Comparative Example 30 | 3 | Comparative Example 6 | 58975 | Gelation |

TABLE 12

| | Unsaturated thiourethane compound | Composition | Compound B Content in Composition ($\times 10^{-4}$ parts by mass) | Viscosity (mPa · sec) |
|---|---|---|---|---|
| Example 20 | 4 | Example 12 | 597 | 0.54 |
| Comparative Example 31 | 5 | Comparative Example 9 | 26578 | Gelation |
| Comparative Example 32 | 6 | Comparative Example 13 | 35687 | Gelation |

As shown in Table 11, in Example 19 in which unsaturated thiourethane compound was prepared by using the composition containing 0.00002 to 2.0 parts by mass of Compound (B) with respect to 100 parts by mass of Compound (A), the unsaturated thiourethane compound 1 having an appropriate viscosity was obtained, and the unsaturated thiourethane compound was successfully prepared.

On the other hand, in Comparative Examples 29 and 30 in which unsaturated thiourethane compounds were prepared by using the compositions containing more than 2.0 parts by mass of the compound (B) with respect to 100 parts by mass of the compound (A), although there was no problem in handling in the stage of raw material, the compound was gelled during the preparation of the unsaturated thiourethane compounds 2 and 3.

As shown in Table 12, in Example 20 in which unsaturated thiourethane compound was prepared by using the composition containing 0.00002 to 2.0 parts by mass of Compound (B) with respect to 100 parts by mass of Compound (A), the unsaturated thiourethane compound 4 having an appropriate viscosity was obtained, and the unsaturated thiourethane compound was successfully prepared.

On the other hand, in Comparative Examples 31 and 32 in which unsaturated thiourethane compounds were prepared by using the compositions containing more than 2.0 parts by mass of the compound (B) with respect to 100 parts by mass of the compound (A), the unsaturated thiourethane compounds 5 and 6 were gelatinized during the preparation of the unsaturated thiourethane compounds 5 and 6, although there was no problem in handling in the raw material stage.

<Example 21> (Reaction Product of Oxime Compound with MOI)

In a 500 ml four-necked flask equipped with a stirrer, reflux condenser and thermometer, 167.0 g of 2-butanone oxime (hereinafter also referred to as "MEK oxime") was charged, and while the temperature was maintained at 35° C., 293.1 g of the composition of Example 6 (The compound (A) is MOI.) was fed and allowed to react for 2 hours to synthesize MOI-BM (2-butanone oxime-O-(carbamoylethyl-2-methacrylate) as an unsaturated butanone oxime compound 1. MOI-BM is a mixture of (2-butanone oxime-O-(E)-(carbamoylethyl-2-methacrylate) and 2-butanone oxime-O—(Z)-(carbamoylethyl-2-methacrylate).

Examples of such MOI-BM products include CARENS MOI-BM (registered trademark).

<Comparative Example 33> (Reaction Product of Oxime Compound with MOI)

An unsaturated butanone oxime compound 2 was synthesized in the same manner as in Example 21 except that the composition of Comparative Example 3 (The compound (A) is MOI.) was used in place of the composition of Example 6.

<Comparative Example 34> (Reaction Product of Oxime Compound with MOI)

An unsaturated butanone oxime compound 3 was synthesized in the same manner as in Example 21 except that the composition of Comparative Example 7 (The compound (A) is MOI.) was used in place of the composition of Example 6.

<Example 22> (Reaction Product of Oxime Compound with AOI)

To a 500 ml four-necked flask equipped with a stirrer, reflux condenser and thermometer, at 15° C., 167.0 g of MEK oxime and 266.7 g of the composition of Example 10 (The compound (A) is AOI.) were fed at the same time and reacted for 1 hour to synthesize AOI-BM (2-butanone oxime-O-(carbamoylethyl-2-acrylate) as the unsaturated butanone oxime compound 4. AOI-BM is a mixture of 2-butanone oxime-O-(E)-(carbamoylethyl-2-acrylate) and 2-butanone oxime-O-(Z)-(carbamoylethyl-2-acrylate).

<Comparative Example 35> (Reaction Product of Oxime Compound with AOI)

An unsaturated butanone oxime compound 5 was synthesized in the same manner as in Example 22 except that the composition of Comparative Example 11 (The compound (A) is AOI.) was used in place of the composition of Example 10.

<Comparative Example 36> (Reaction Product of Oxime Compound with AOI)

An unsaturated butanone oxime compound 6 was synthesized in the same manner as in Example 22 except that the composition of Comparative Example 15 (The compound (A) is AOI.) was used in place of the composition of Example 10.

The viscosities of the reaction liquids containing the unsaturated butanone oxime compounds 1 to 6, obtained in Examples 21 and 22 and Comparative Examples 33 to 36, were measured in accordance with JIS-Z 8803: 2011 at 25° C. using a tuning-fork-type vibrating viscometer (SV type viscometer manufactured by A & D Co., Ltd. (SV-10 Type)). The results are shown in Tables 13 and 14.

TABLE 13

|  | Unsaturated Butanone Oxime compound | Composition | Compound B Content in Composition ($\times 10^{-4}$ parts by mass) | Viscosity (mPa · sec) |
| --- | --- | --- | --- | --- |
| Example 21 | 1 | Example 6 | 623 | 0.15 |
| Comparative Example 33 | 2 | Comparative Example 3 | 24006 | Gelation |
| Comparative Example 34 | 3 | Comparative Example 7 | 35687 | Gelation |

TABLE 14

|  | Unsaturated Butanone Oxime compound | Composition | Compound B Content in Composition ($\times 10^{-4}$ parts by mass) | Viscosity (mPa · sec) |
| --- | --- | --- | --- | --- |
| Example 22 | 4 | Example 10 | 654 | 0.22 |
| Comparative Example 35 | 5 | Comparative Example 1 | 28674 | Gelation |

TABLE 14-continued

| | Unsaturated Butanone Oxime compound | Composition | Compound B Content in Composition (×10⁻⁴ parts by mass) | Viscosity (mPa · sec) |
|---|---|---|---|---|
| Comparative Example 36 | 6 | Comparative Example 15 | 37885 | Gelation |

As shown in Table 13, in Example 21, in which unsaturated butanone oxime compounds were prepared by using the composition containing 0.00002 to 2.0 parts by mass of the compound (B) with respect to 100 parts by mass of the compound (A), the unsaturated butanone oxime compound 1 having proper viscosity were obtained, and the unsaturated butanone oxime compounds were successfully prepared.

On the other hand, in Comparative Examples 33 and 34 in which an unsaturated butanone oxime compound was prepared by using the compositions containing more than 2.0 parts by mass of the compound (B) with respect to 100 parts by mass of the compound (A), although there was no problem in handling in the stage of raw material, the compound gelled during the preparation of the unsaturated butanone oxime compounds 2 and 3.

As shown in Table 14, in Example 22, in which unsaturated butanone oxime compounds were prepared by using the composition containing 0.00002 to 2.0 parts by mass of the compound (B) with respect to 100 parts by mass of the compound (A), the unsaturated butanone oxime compound 4 having the proper viscosity were obtained, and the unsaturated butanone oxime compounds were successfully prepared.

On the other hand, in Comparative Examples 35 and 36, in which an unsaturated butanone oxime compound were prepared by using the composition containing more than 2.0 parts by mass of the compound (B) with respect to 100 parts by mass of the compound (A), although there was no problem in handling in the stage of raw material, the compound gelled during the preparation of the unsaturated butanone oxime compounds 5 and 6.

As shown in the above results, depending on whether or not the content of the compound (B) with respect to 100 parts by mass of the compound (A) was 0.00002 to 2.0 parts by mass, there was a large difference in the behavior of the composition during storage. The viscosity of the unsaturated compound obtained by reacting the composition with any one of (poly)ol, (poly)amine, (poly)carboxylic acid, (poly)thiol and oxime compound also differed greatly depending on whether or not the content of the compound (B) with respect to 100 parts by mass of the compound (A) in the composition was 0.00002 to 2.0 parts by mass.

From these results, it was confirmed that the concentration of compound (B) in the composition is useful as an index for determining the stability of the composition during storage and as an index for determining whether or not a rapid increase in viscosity and/or gelation occurs during production when the unsaturated compound is produced by using the composition as a raw material.

INDUSTRIAL APPLICABILITY

According to the present invention, the stability during storage and the stability during transportation of the composition containing the unsaturated isocyanate compound can be improved.

The invention claimed is:

1. A composition comprising:
a compound (A) represented by general formula (1) and
a compound (B) represented by general formula (2),
wherein the composition comprises 0.00002 to 2.0 parts by mass of the compound (B) with respect to 100 parts by mass of the compound (A),

wherein in the general formulae (1) and (2),
$R_1$ is an ethylenically unsaturated group having 2 to 7 carbon atoms;
$R_2$ is a (m+n)-valent hydrocarbon group having 1 to 7 carbon atoms and optionally comprises an ether group;
$R_1$ and $R_2$ in the general formula (1) are the same as $R_1$ and $R_2$ in the general formula (2); and
n and m each represent an integer of 1 or 2.

2. The composition according to claim 1, wherein the compound (A) is at least one compound selected from the group consisting of 2-methacryloyloxyethyl isocyanate, 2-(isocyanatoethyloxy) ethyl methacrylate, 2-acryloyloxyethyl isocyanate, 2-(isocyanatoethyloxy) ethyl acrylate, and 1,1-bis(acryloyloxymethyl)ethyl isocyanate.

3. The composition according to claim 1, wherein a content of the compound (A) in the composition is 95.0% by mass or more.

4. The composition according to claim 1, wherein the content of the compound (A) in the composition is 97.0% by mass to 99.9% by mass.

5. The composition according to claim 1, further comprising as an additive any one selected from the group consisting of hydroquinone, methoxyhydroquinone, catechol, p-tert-butylcatechol, cresol, 2,6-di-tert-butyl-4-methylphenol (BHT), and phenothiazine.

6. A method of producing an unsaturated compound, comprising the steps of:
mixing the composition according to claim 1 with a compound having active hydrogen; and
reacting the compound (A) contained in the composition with the compound having active hydrogen to obtain a reaction product.

7. The method of producing an unsaturated compound according to claim 6, wherein the compound having the active hydrogen is an alcohol, a thiol, an amine or a carboxylic acid.

8. The method of producing an unsaturated compound according to claim 6, wherein the reaction product is an unsaturated urethane compound, an unsaturated thiourethane compound, an unsaturated urea compound, or an unsaturated amide compound.

9. The method of producing an unsaturated compound according to claim 6, wherein the reaction product is any one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

10. The method of producing an unsaturated compound according to claim 6, wherein a reaction temperature at which the compound (A) contained in the composition is reacted with the compound having the active hydrogen is −10 to 100° C.

* * * * *